US006974441B2

(12) United States Patent
Ravo

(10) Patent No.: US 6,974,441 B2
(45) Date of Patent: Dec. 13, 2005

(54) INFLATABLE INTRALUMINAL MOLDING DEVICE

(76) Inventor: Biagio Ravo, Rome (IT)

( * ) Notice: Subject to any disclaimer, the term of this patent is extended or adjusted under 35 U.S.C. 154(b) by 1 day.

(21) Appl. No.: 10/825,544

(22) Filed: Apr. 15, 2004

(65) Prior Publication Data

US 2004/0199196 A1 Oct. 7, 2004

Related U.S. Application Data

(63) Continuation of application No. 09/817,956, filed on Mar. 27, 2001, now abandoned, which is a continuation of application No. 09/245,788, filed on Feb. 5, 1999, now abandoned.
(60) Provisional application No. 60/073,902, filed on Feb. 6, 1998.

(51) Int. Cl.[7] .............................................. A61M 29/00
(52) U.S. Cl. ................................................. 604/101.01
(58) Field of Search ....................... 604/101.01, 101.03, 604/101.05, 103, 96.01; 606/190, 191, 192

(56) References Cited

U.S. PATENT DOCUMENTS 5,951,514 A * 9/1999 Sahota ................... 604/101.05

* cited by examiner

Primary Examiner—Kevin C. Sirmons
(74) Attorney, Agent, or Firm—24 Ip Law Group USA, PLLC; Timothy R. DeWitt

(57) ABSTRACT

An intraluminal device has an elongated body member having a series of independent inflatable sections along its length. At least one inflating/deflating line extends from each inflatable section to a distal end of the body member. The device may be used for positing, isolating or identifying a lumen by giving shape to a collapsed viscus. The device may also be used to visualize intraluminal structure or control pressure within a hollow viscus from within the hollow viscus.

10 Claims, 3 Drawing Sheets

INFLATABLE INTRALUMINAL MOLDING DEVICE

This application is a continuation of U.S. patent application Ser. No. 09/817,956 filed on Mar. 27, 2001 now abandoned, which was a continuation of U.S. patent application Ser. No. 09/245,788 filed on Feb. 5, 1999 now abandoned and claims the benefit of U.S. Provisional Patent Application Ser. No. 60/073,902 entitled "Inflatable Intraluminal Molding Device", filed Feb. 6, 1998.

BACKGROUND OF THE INVENTION

1. Field of the Invention

I, Biagio Ravo, have invented a surgical and diagnostic device which relates to an inflatable intraluminal molding device for positioning, isolating and/or identifying relevant segments of a hollow viscous during surgical or diagnostic procedures.

2. Background Information

During operations on any hollow viscus, such as colorectal surgery, gastrointestinal surgery, urological or biliary surgery, it is often necessary to position, isolate and/or identify relevant segments of the hollow viscus being operated upon. It would be additionally advantageous to perform the positioning, isolation and/or identifying procedure from internally of the hollow viscus.

It is an object of the present invention to provide an inflatable intraluminal surgical device for positioning, isolation and/or identification of the hollow viscus for use internally of the hollow viscus to give shape to the collapsed viscus by acquiring its distended form. A further object of the present invention is to provide an intraluminal surgical and diagnostic device independently operable at several locations within a hollow viscus. Another object of the present invention is to provide a device to maintain the lumen of the hollow viscus clear of fluid and/or air. A further object of the present invention is to provide a device which can assist in identifying perforations or leaks in a hollow viscus, assist in visualizing intraluminal structure and control pressure within an internal viscus. A further object of the present invention is to provide an intraluminal surgical and diagnostic device which is easy to manufacture and simple to use and operate.

SUMMARY OF THE INVENTION

The objects of the present invention are achieved with an inflatable intraluminal surgical device according to the present invention. The surgical device according to the present invention includes an elongated body member with a plurality of independent inflatable balloon sections extending along the length of the body member, and a mechanism for independently inflating each individual balloon section along the length of the body member.

The elongated body member may be in the form of a sleeve which is adapted to fit over an existing scope and/or suction tube. The mechanisms for individually inflating the specific balloon sections may be formed as individual air/fluid lines extending from each balloon section along the body member to a distal end of the body member. The individual balloon sections may be formed such that they conform to the specific anatomical structure when inflated. One or more suction tubes and/or optical scopes may be positioned at various locations along the body member between adjacent balloon sections. Leads from the individual scopes and suction tubes will extend along the body member to the distal end of the device for appropriate connection to a suction source or video display equipment as known in the art. The suction tubes may also be used to supply medicine or irrigation fluid to selected portions of the hollow viscus.

These and other advantages of the present invention will be clarified in the brief description of the preferred embodiments taken together with the attached figures wherein like reference numerals represent like elements throughout.

BRIEF DESCRIPTION OF THE PREFERRED EMBODIMENTS

Figure 1:
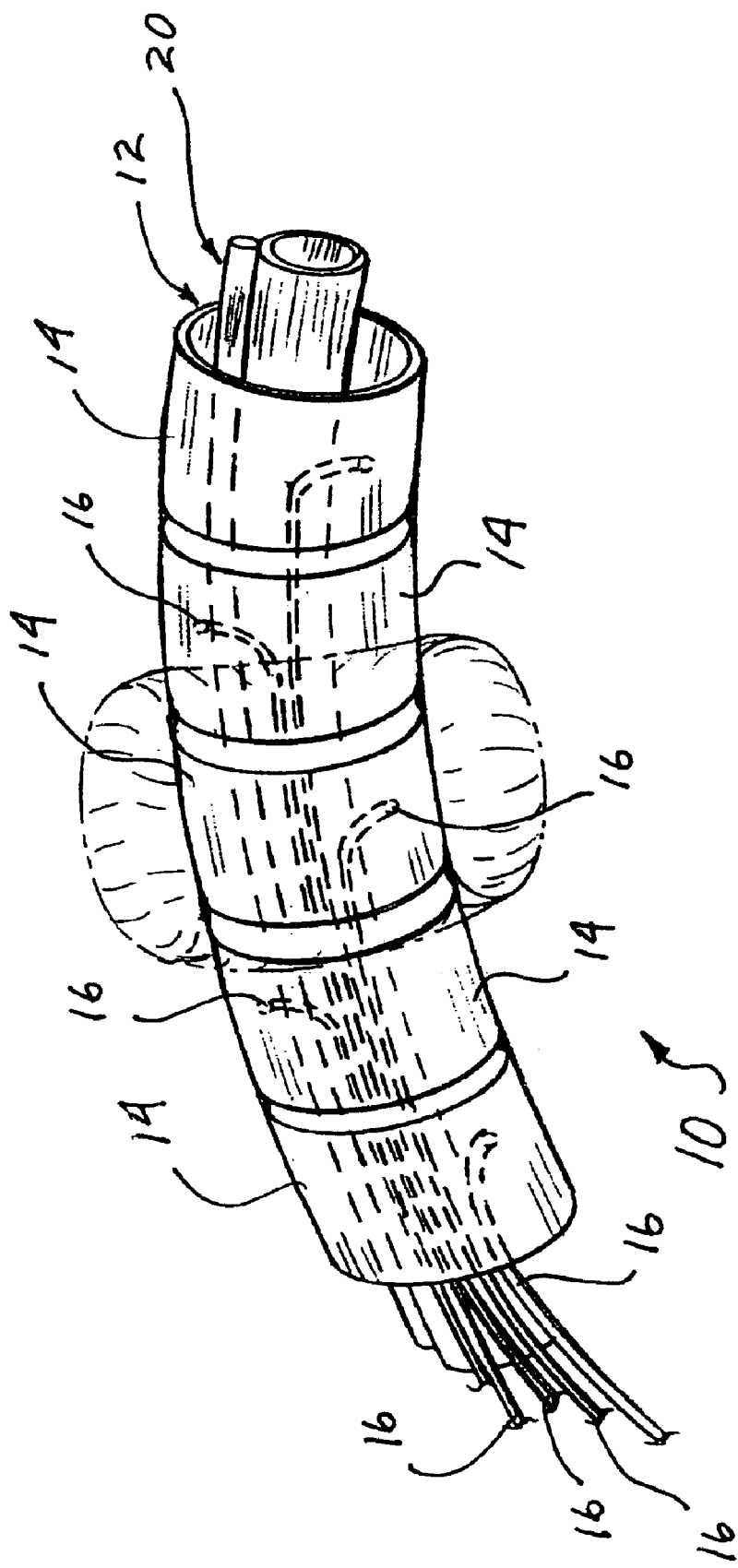
FIG. 1 schematically illustrates an inflatable intraluminal surgical device according to a first embodiment of the present invention.

FIG. 1 schematically illustrates an inflatable intraluminal surgical and diagnostic device 10 according to the present invention. The surgical device 10 includes an elongated body member formed as a sleeve 12. Along the length of the sleeve 12 are a plurality of independent balloon sections 14. Individual air lines 16 extend from each balloon section 14 along the sleeve 12 to the distal control end of the device 10. The individual air lines 16 may be color coded, numbered or include other appropriate indicia to indicate which specific balloon section 14 along the length of sleeve 12 the specific airline 16 is associated with.

The sleeve 12 is adapted to fit around an existing suction tube and scope member 20. The leading end of the sleeve 12 may include appropriate conventional connecting mechanisms to attach the leading end of the sleeve 12 to the leading end of the suction tube and scope member 20 in the position generally shown in FIG. 1.

In operation, the surgical device 10 is positioned on the suction tube and scope member 20 by sliding sleeve 12 along the suction tube and scope member 20 and attaching the leading end of the sleeve 12 to a leading end of the suction tube and scope member 20 through a connecting mechanism. The surgical device 10, along with the existing suction tube and scope member 20, can be inserted into the specific hollow viscus, such as the colon. With the surgical device 10 inserted into the colon, a desired segment of the colon can be isolated by inflating the specific balloon section 14 associated with that segment. The balloon section 14 can be inflated with air and/or fluid injected through the appropriate air line 16. The injection may be through the use of a syringe or any appropriate inflation device. The balloon sections 14 may also be deflated through use of air lines 16. The inflated balloon section 14 will conform to the colon section and will expand the colon section serving to isolate and identify the specific section. The segment associated with the inflated balloon section 14 (one of which is shown in phantom in FIG. 1) can be easily identified and positioned from the exterior for appropriate operations. The surgical device 10 may be utilized for isolating a section of a hollow viscus to be operated upon, such as a section of colon to be resected, which is between a pair of inflated, spaced balloon sections 14 along the surgical device 10. The surgical device 10 may also be used to control bleeding along the length of a hollow viscus. There are many independent applications for the surgical device 10 of the present invention.

Figure 2:
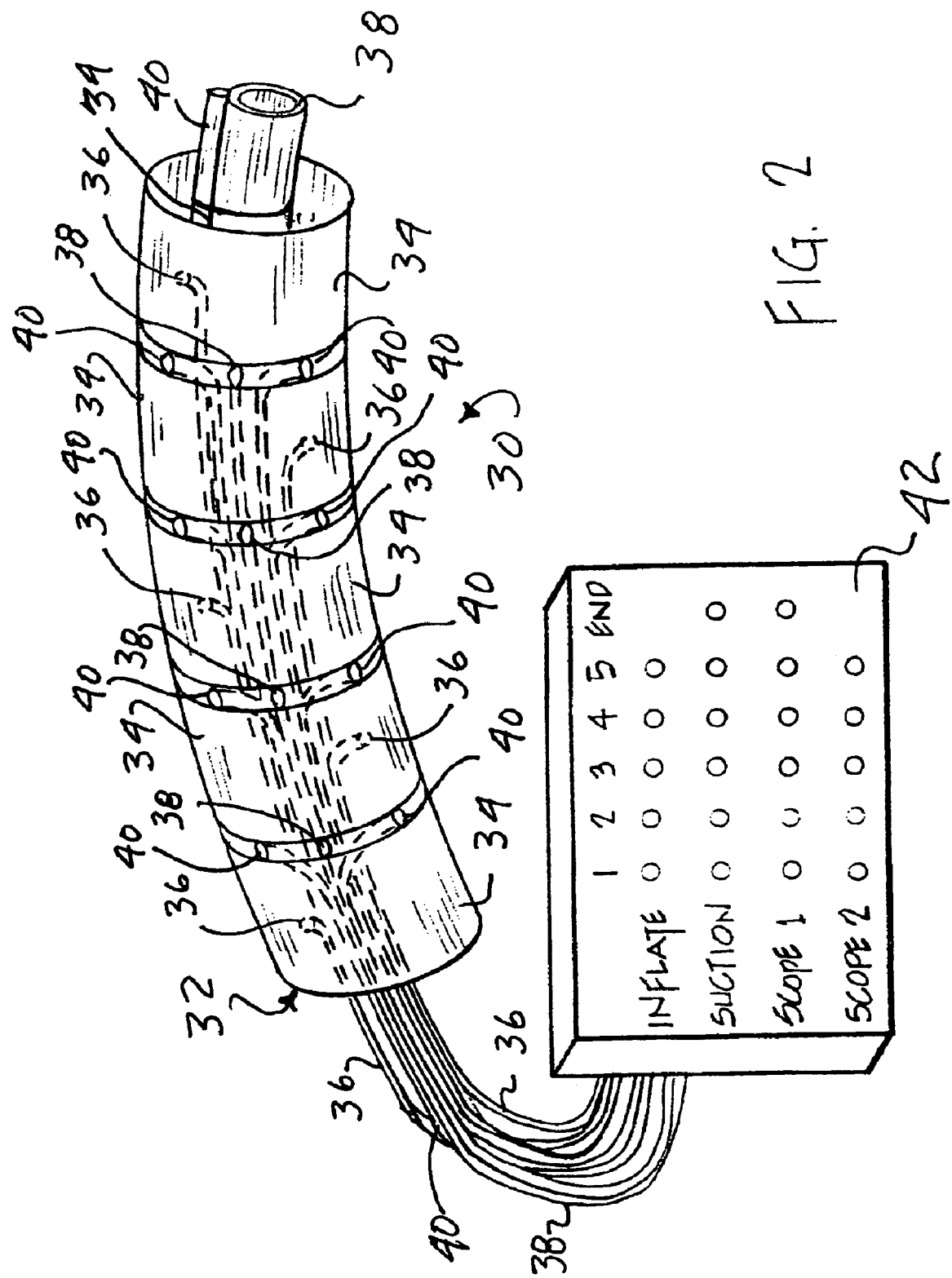
FIG. 2 schematically illustrates an inflatable intraluminal surgical device according to a second embodiment of the present invention.

FIG. 2 schematically illustrates a surgical device 30 according to a second embodiment of the present invention. The surgical device 30 is similar to the surgical device 10 and includes a body member 32 with a plurality of independently inflatable/deflatable balloon sections 34 along the length of body member 32. Individual air lines 36 extend from each balloon section 34 along the body member 32. The surgical device 30 additionally includes suction tubes 38 extending from the leading end of the body member 32 and also positioned between adjacent balloon sections 34. The surgical device 30 further includes optical fibers 40 extending from the leading end of the body member 32 and also positioned between adjacent balloon sections 34. The optical fibers 40 between adjacent balloon sections 34 are illustrated extending in opposite directions relative to the body member 32 to provide a comprehensive view to the surgeon, or operator. The air lines 36, suction tubes 38 and optical fibers 42 extend along the body member 32 to an external control panel 42. The control panel 42 allows the specific air lines 36, suction tubes 38 or optical fibers 40 to be accessed as desired.

In operation, the surgical device 30 operates similar to the surgical device 10 above with the surgical device 30 inserted into an appropriate hollow viscus, such as a colon, gastrointestinal track or the like. The specific balloon section 34, or plurality of balloon sections 34, can be independently inflated and deflated by accessing the associated air line 36 on control panel 42. As discussed above, the balloon section 34 can be filled with air through air line 36 or fluid, such as saline or the like, through air line 36. Additionally, suction tubes 38 allow for specific sections along the length of the surgical device 30 to be suctioned or for medication or other fluid to be introduced to specific sections along the length of the surgical device 30. For example, a pair of spaced balloon sections 34 may be inflated to isolate a colon section therebetween which is to be filled with a specific liquid applied through appropriate suction tube 38. The surgeon can view the desired location along the surgical device 30 by connecting the appropriate optical fibers 40 to visual equipment through connections to control panel 42 in a known manner. As discussed above in connection with surgical device 10, there are many applications, both surgical and diagnostic, for the surgical device 30 of the present invention.

Figure 3:
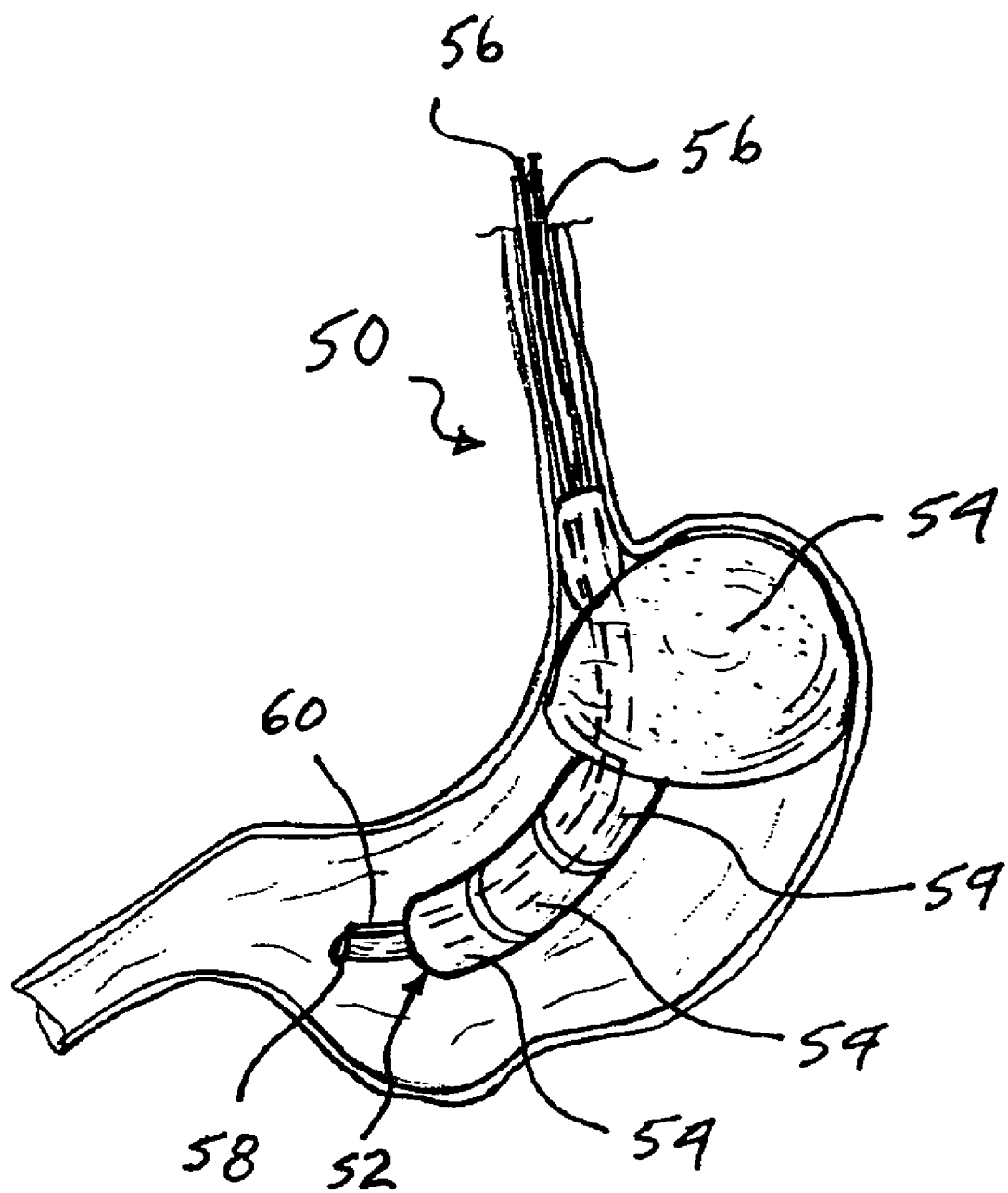
FIG. 3 schematically illustrates an inflatable intraluminal surgical device according to a third embodiment of the present invention.

FIG. 3 schematically illustrates a surgical device 50 according to a third embodiment of the present invention. Surgical device 50 is substantially similar to surgical devices 10 and 30 described above and includes an elongated body member 52 with a plurality of spaced balloon sections 54 along the length thereof. Individual air lines 56 extend to these individual balloon sections 54 along the body member 52 in substantially the same manner discussed above in connection with surgical devices 10 and 30. The surgical device 50 is illustrated with a suction tube 58 and an optical fiber 60 extending to the end of the surgical device 50 and may further include suction tubes and optical fibers with the air lines 56 and suction tubes and optical fibers attached to a control panel similar to that discussed above in connection with surgical device 30. The surgical device 50 is designed for a gastrointestinal operation and illustrates that the specific balloon sections 54, when inflated, are designed to conform to the specific anatomical structure. As discussed above, the surgical device 50 of the present invention can be utilized in a wide variety of procedures, both surgical and diagnostic. The device 50 can maintain the desired size and intraluminal pressure on the esophagus eliminating other tubes and dilators currently used.

Any of the devices 10, 30 and 50 of my invention can be used to help identify lumen perforations, isolate lumen segments, control lumen pressure, control and prevent bleeding into the lumen, medicate and/or suction selected portions of the lumen, visualize inner lumen structure and a variety of other applications. Further, it would be apparent to those of ordinary skill in the art that various modifications may be made to the present invention without departing from the spirit and scope thereof. For example, the devices 10, 30 or 50 may be used with a reusable light source to assist the operation. The scope of the present invention is defined by the appended claims and equivalents thereto.

What is claimed is:

1. An intraluminal device for insertion in a hollow viscus, comprising:

an elongated body member, the elongated body member having at least three independent inflatable sections along the length of the body member, wherein the independent sections are axially spaced along the body member with one of said at least three inflatable sections extending to a distal end of said body member and a second of said at least three inflatable sections extending to a proximal end of said body member and each inflatable section is axially fixed relative to the remainder of the axially spaced inflatable sections, and wherein each inflatable section is designed to give shape to a collapsed viscus by acquiring its distended form when the inflated section is in the inflated condition;

at least one tube within said body member wherein each adjacent inflatable section extends around the entire circumference of body member, and wherein the tube has an opening at one end thereof positioned at a peripheral portion of the device between the adjacent inflatable sections, and wherein the tube extends from the opening at the one end to a proximal end of the body member, wherein the tube is adapted to be selectively attached to a suction source or a fluid supply source whereby material can be selectively withdrawn from or supplied to the area surrounding the device and within the hollow viscus between the adjacent inflatable sections with the material flowing through the tube opening at the end of the tube;

means for independently inflating each individual inflatable section to give shape to a collapsed viscus by acquiring its distended form when the inflatable section is in the inflated condition; and at least one optical scope positioned between adjacent inflatable sections and extending to a proximal end of the body member whereby an operator may view the section of the hollow viscus between the adjacent sections.

2. The device of claim 1 wherein the body member is a sleeve which is adapted to fit over an existing intraluminal tool.

3. The device of claim 2 wherein the means for independently inflating each inflatable section includes individual fluid lines extending from each inflatable section to a proximal end of the body member.

4. The device of claim 1 wherein the means for independently inflating each inflatable section includes individual fluid lines extending from each inflatable section to a proximal end of the body member.

5. The device of claim 1 further including a control panel, wherein each fluid line, tube and optical scope is attached to the control panel.

6. The device of claim 1 wherein individual inflatable sections are adapted to conform to specific anatomical structures.

7. The device of claim 1 wherein each inflatable section is generally a cylindrical shape.

8. The device of claim 1 further including an end tube extending the length of the body, wherein the end tube has an opening at one end thereof positioned at an end of the device, wherein the end tube is adapted to be selectively attached to a suction source or a fluid supply source whereby material can be selectively withdrawn from or supplied to the area immediately beyond the device and within the hollow viscus with the material flowing through the end of the tube opening at the end of the end of the tube.

9. An intraluminal device for insertion in a hollow viscus, comprising:

an elongated body member, the elongated body member having at least three independent inflatable sections alone the length of the body member, wherein the independent sections are axially spaced along the body member with one of said at least three inflatable sections extending to a distal end of said body member and a second of said at least three inflatable sections extending to a proximal end of said body member and each inflatable section is axially fixed relative to the remainder of the axially spaced inflatable sections, and wherein each inflatable section is designed to give shape to a collapsed viscus by acquiring its distended form when the inflated section is in the inflated condition;

at least one tube within said body member wherein each adjacent inflatable section extends around the entire circumference of body member, and wherein the tube has an opening at one end thereof positioned at a peripheral portion of the device between the adjacent inflatable sections, and wherein the tube extends from the opening at the one end to a proximal end of the body member, wherein the tube is adapted to be selectively attached to a suction source or a fluid supply source whereby material can be selectively withdrawn from or supplied to the area surrounding the device and within the hollow viscus between the adjacent inflatable sections with the material flowing through the tube opening at the end of the tube;

means for independently inflating each individual inflatable section to give shape to a collapsed viscus by acquiring its distended form when the inflatable section is in the inflated condition; and at least one optical scope positioned to extend the length of the body member whereby an operator may view the section of the hollow viscus immediately beyond the device.

10. An intraluminal device for insertion in a hollow viscus, comprising:

an elongated body member, the elongated body member having a plurality of inflatable sections along the length of the body member, wherein the inflatable sections are axially spaced along the body member and each inflatable section is axially fixed relative to the remainder of the axially spaced inflatable sections, and wherein each inflatable section is designed to give shape to a collapsed viscus by acquiring its distended form when the inflated section is in the inflated condition;

at least one suction tube positioned between adjacent inflatable sections, and wherein said suction tube has an opening at one end thereof positioned at a peripheral portion of the device between the adjacent inflatable sections, and wherein said suction tube extends from the opening at the one end to a proximal end of the body member, wherein said suction tube is adapted to be selectively attached to a suction source or a fluid supply source whereby material can be selectively withdrawn from or supplied to the area surrounding the device and within the hollow viscus between the adjacent inflatable sections with the material flowing through the tube opening at the end of said suction tube;

a first inflation tube for supplying a fluid to inflate a first one of said inflatable sections to give shape to a collapsed viscus by acquiring its distended form when the inflatable section is in the inflated condition;

a second inflation tube for supplying a fluid to inflate a second one of said inflatable sections to give shape to a collapsed viscus by acquiring its distended form when the inflatable section is in the inflated condition; and at least one optical scope positioned between said first and second inflatable sections and extending to a proximal end of the body member whereby an operator may view the section of the hollow viscus between said first and second adjacent sections.

* * * * *